United States Patent [19]
Junginger et al.

[11] 3,967,107
[45] June 29, 1976

[54] OPERATING THEATER LIGHT

[75] Inventors: Klaus Junginger, Rodenbach; Walter Sturm, Hanau, both of Germany

[73] Assignee: Original Hanau Quarzlampen GmbH, Hanau, Germany

[22] Filed: Oct. 5, 1973

[21] Appl. No.: 403,895

[30] Foreign Application Priority Data

Oct. 7, 1972 Germany............................ 2249347

[52] U.S. Cl................................ 240/1.4; 240/41.15
[51] Int. Cl.².................... A61G 13/00; F21V 33/00
[58] Field of Search.......................... 240/1.4, 41.15; 250/201, 215

[56] References Cited
UNITED STATES PATENTS 3,110,815  11/1963  Sturm .............................. 240/1.4 A
3,375,362  3/1968  Klippert.............................. 240/1.4

*Primary Examiner*—Richard M. Sheer
*Attorney, Agent, or Firm*—Irving M. Weiner; Pamela S. Burt

[57] ABSTRACT

An illumination system for an operating theater having a pinpointing spotlamp and several individual satellite spotlamps all of which are pivotable independently of each other in two mutually-perpendicular directions. The pinpointing spotlamp is adjustable to select a desired area to be illuminated, and each satellite spotlamp is provided with a photoelectric servomechanism which operates in response to light from the area illuminated by the pinpointing spotlamp to adjust the associated satellite spotlamp.

1 Claim, 4 Drawing Figures

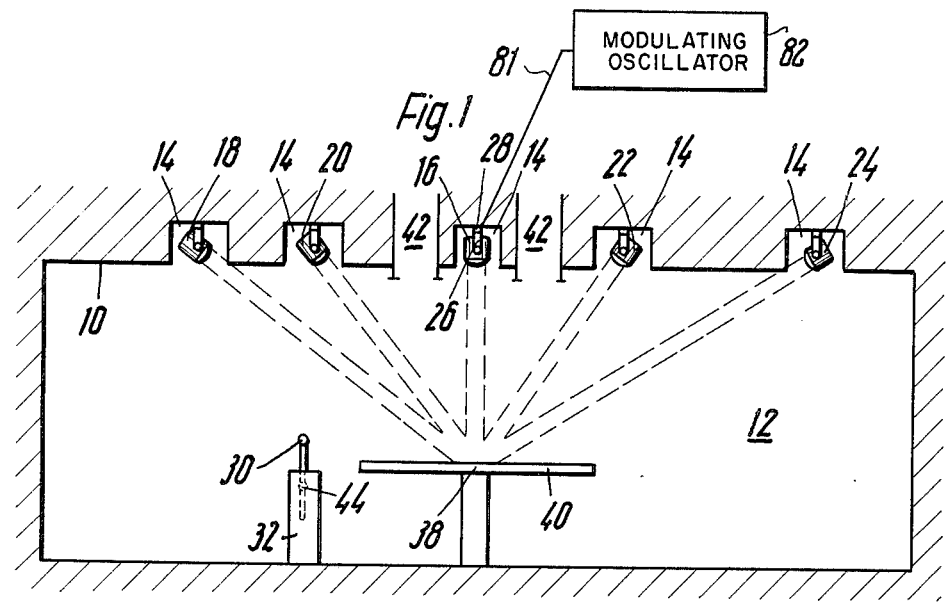
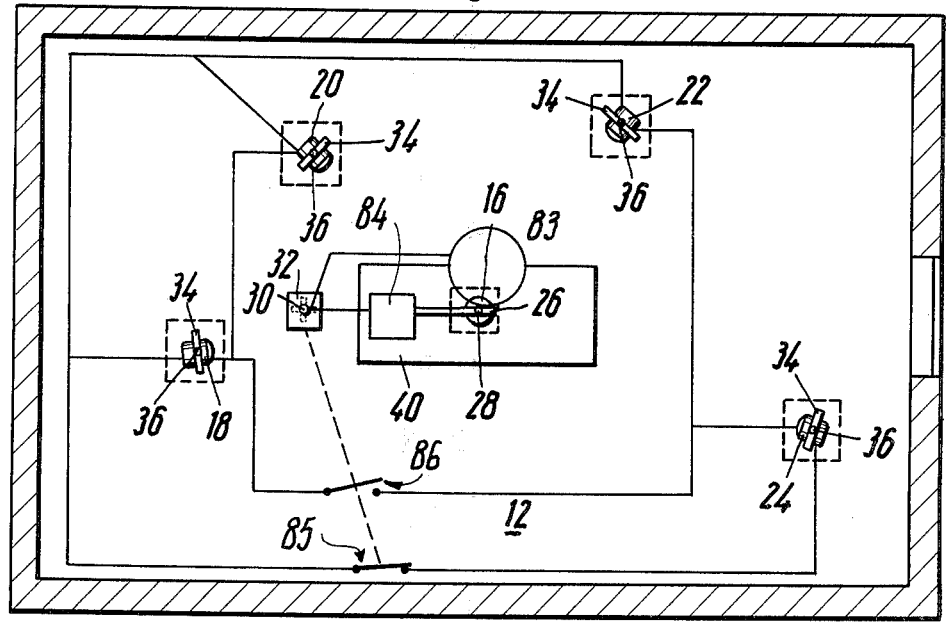

OPERATING THEATER LIGHT

The present invention relates generally to an illumination system, and in particular to an operating theater light with several individual stoplamps.

BACKGROUND OF THE INVENTION

Heretofore, a theater light is known in which several individual spotlamps are arranged in a common housing which is suspended in such a fashion as to be able to swivel about two axes. The light cones produced by the individual spotlamps meet approximately on the axis of symmetry of the overall light. The theater light is provided with a photoelectric follow-up control which aligns the axis of symmetry of the light on the light of a portable lamp used to select the operation zone to be illuminated. A follow-up control provided in respect of each axis of rotation consists of two photoelectric cells followed by amplifiers and relays by means of which the direction and speed of rotation of a motor assigned to each axis can be adjusted, the motor rotating the common housing of the theater light.

Another known theater light which is fixed to the ceiling consists of several individual spotlamps arranged in a distributed fashion, which can be commonly aligned on an operation zone. The individual spotlamps are connected together through control linkages. In setting up the spotlamps on an operation zone, the individual lamps rotate in two mutually-perpendicular directions, through different angles, so that their light cones strike the operation zone.

One object of the present invention is to develop in respect of the operation light introductorily described, an arrangement by means of which the individual spotlamps can be set up in an operating theater at the best positions to produce shadow-free illumination of operation zones, thus without hindering or undesirably impairing the use or function of other equipment or devices located in the operating theater.

SUMMARY OF THE INVENTION

The present invention provides an illumination system including a plurality of spotlamps each of which is separately and independently pivotably mounted so that each spotlamp may move independently of one another. The plurality of spotlamps includes a pinpointing spotlamp and several individual satellite spotlamps. The pinpointing spotlamp is adjustable to select a desired area to be illuminated. Each of the individual satellite spotlamps is provided with a photoelectric servomechanism which operates in response to light from the area illuminated by the pinpointing spotlamp to adjust the associated satellite spotlamp.

In accordance with one possible embodiment of the invention, there is provided a pinpointing spotlamp which may be manually adjustable to select a desired area of illumination and the other spotlamps are suspended pivotably independently of one another, preferably so that they can pivot in two mutually-perpendicular directions, and can be adjusted by means of photoelectric follow-up systems to which the area illuminated by the pinpointing spotlamp can be applied as a setpoint value.

A major advantage of the arrangement resides in its creation of optimum illumination for operating theaters into which, from the ceiling, a bacteria-free, laminar airflow is directed onto the operating table in order to ensure that operations are carried out substantially in a bacteria-free environment. The theater lights thus far known are not suitable for use in so-called "White rooms" of this kind because they either take up the space required on the ceiling for the air inlet orifice or deflect the entering air and thus impair the intended action. The arrangement in accordance with the invention on the other hand, furthermore enables good deep illumination of cavities extending obliquely into the body to be achieved.

In a preferred embodiment, it is arranged that the pinpointing spotlamp is suspended so that it can swivel in two mutually-perpendicular directions and can be adjusted through the medium of a control lever by means of which, when pivoted out of its rest position, the illumination produced by the other spotlamps can be switched off and the follow-up system switched on.

By switching off the other spotlamps during setting up on the area illuminated by the pinpointing spotlamp, this arrangement advantageously avoids the nuisance of reflected rays from the other spotlamps affecting the adjustment.

In one convenient embodiment, the light radiated by the pinpointing spotlamp is modulated, whilst the follow-up systems contain circuits tuned to the modulation in the emitted light. One advantage of this arrangement is its insensitivity to daylight or to other light sources modulated at different frequencies. Through the modulation of the light produced by the pinpointing spotlamp at a frequency higher than 100 cycles per second the follow-up circuits are protected against influencing by ordinary incandescent bulbs or fluorescent tubes.

One convenient embodiment resides in the fact that the pinpointing spotlamp is arranged substantially vertically above an operating table, whilst the remaining spotlamps are disposed at varying distances and/or angles from the operating table.

BRIEF DESCRIPTION OF THE DRAWINGS

FIG. 1 illustrates a theater light or illumination system according to a first embodiment of the invention schematically in side elevation.

FIG. 2 illustrates the arrangement of FIG. 1 in plan view.

DETAILED DESCRIPTION

Figure 3:
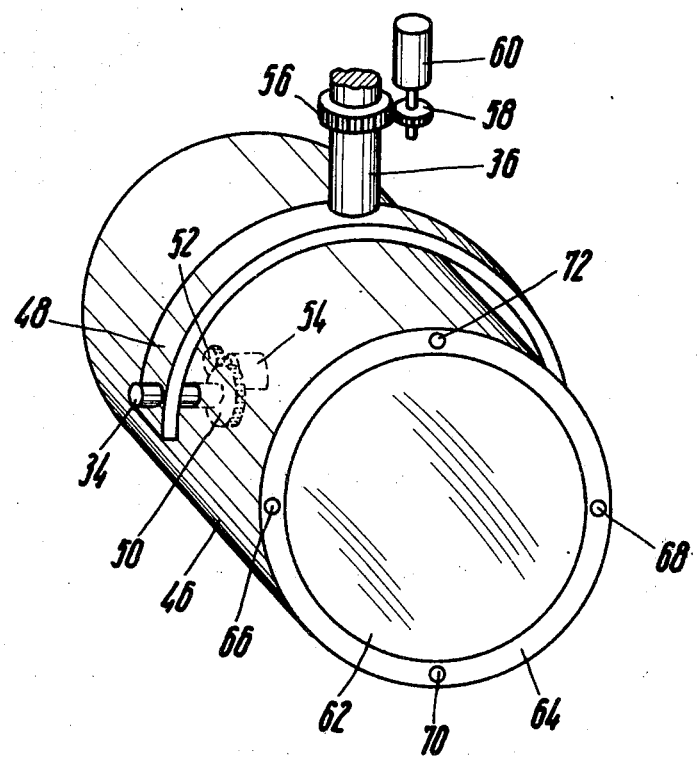
FIG. 3 illustrates an individual satellite spotlamp with its associated suspension arrangements.

With reference to FIG. 1, in the ceiling 10 of an operating theater 12, there are box-like recesses 14 in which a pinpointing spotlamp 16 and individual satellite spotlamps 18, 20, 22 and 24 are arranged. The pinpointing spotlamp 16 is suspended in order to be able to swivel about two mutually-perpendicular axes 26 and 28. The pinpointing spotlamp 16 is imparted a rotary motion by means of two electric motors which have not been shown in detail, but which can be switched on and off by a control lever 30 arranged upon a console 32 in the operating theater 12.

The individual spotlamps 18, 20, 22 and 24 are suspended in order to be able to swivel about mutually-perpendicular axes 34 and 36 under the control of a photoelectric servomechanism. Each axis of each of the individual spotlamps 18, 20, 22 and 24 is assigned a photoelectric follow-up system which is provided by way of setpoint value with the area 38 illuminated by the pinpointing spotlamp 16 on an operation zone.

Whereas the pinpointing spotlamp 16 is arranged substantially perpendicularly above an operating table 40, the individual spotlamps 18 to 24 have differing distances from the operating table 40. Because of these distances, the lightbeams directed by the individual spotlamps 18, 20, 22 and 24 onto the illuminated area 38 have different angles of incidence. The different angles of incidence prevent any shadowing in an operation zone, and furthermore make it possible to effect deep illumination of incisions or cavities extending obliquely into a patient's body.

The dimensions of the spotlamps 16 to 24 are small. Consequently, the recesses 14 can be made small as well. Because the spotlamps 16 to 24 are not attached to one another by levers and/or linkages, and are furthermore suspended from the ceiling 10 independently of one another, there is no disturbance to any other devices required in the operating theater 12, such as airducts 42 through which sterile air is fed under laminar flow conditions into the theater 12 in order to enable substantially sterile operating conditions to be achieved.

The installation positions of the spotlamps 18 to 24 are therefore determined primarily by the desired angles of incidence of the lightbeams which are intended to illuminate the area 38 in a shadow-free fashion, said area 38 being displaceable arbitrarily within the confines of the operating table 40, by appropriate control of the pinpointing spotlamp 16. The simple and compact arrangement and assembly of the spotlamps 18 to 24 makes it possible to use a large number of such lamps so that the lighting problem can be resolved in an optimum manner.

The control lever 30 can be provided with a spherical section 44 which is carried in a correspondingly-shaped bearing in order to enable it to pivot in different directions. With pivoting of the control lever 30, contacts can be operated by means of which the motors (not shown) for the axes 26 and 28 of the pinpointing spotlamp 16 can be supplied. Through the medium of the polarity of the voltage applied to the motors associated with the axes 26 and 28, their directions of rotation can be controlled.

The control lever 30 also operates switches which have not been shown. One switch, which is closed when the control lever 30 is in the inoperative condition, and is opened when it is pivoted, serves to supply the voltage to the bulbs in the spotlamps 18 to 24. Another switch, which is open when the control lever 30 is in the inoperative position, and closed when it is pivoted, is arranged in the supply lead to the follow-up control systems for the lamps 18 to 24. The voltage supply to the bulb in the pinpointing spotlamp 16 is not affected by the control lever 30.

The bulb in the pinpointing spotlamp 16 is supplied from an oscillator (not shown) which produces a voltage with a frequency in excess of 100 cycles per second. The voltage can have a frequency of about 400 cycles per second. However, frequencies of several kHz are equally possible.

With reference to FIG. 3, the spotlamps 18 to 24 have a housing 46 to which a horizontal axis or pivot 34 is attached, this being rotatably assembled in a yoke 48. The vertical axis or pivot 36 is rigidly fixed to the yoke 48. The pivot 34 is provided with a gear 40 meshing with a gear 52 carried upon the spindle of a servomotor 54 arranged inside the housing 46.

The pivot 36 carries a gear 56 meshing with a gear 58 attached to the rotor of a servomotor 60 arranged on the ceiling 10. The pivot 36 is rotatably assembled in a bearing (not shown) which is assembled on the ceiling 10.

Inside the housing 46 there is a bulb (not shown in detail), the light rays from which are directed by a reflector and a spotlamp glass 62 into the operating theater 12. At one edge 64, near the spotlamp glass 62, photosensitive elements, e.g., photoelectric cells 66, 68, 70 and 72, are arranged.

The photoelectric cells 66 and 68 supply a follow-up control circuit which controls the motor 60. The photoelectric cells 70 and 72 are connected to a follow-up control circuit which drives the motor 54.

Figure 4:
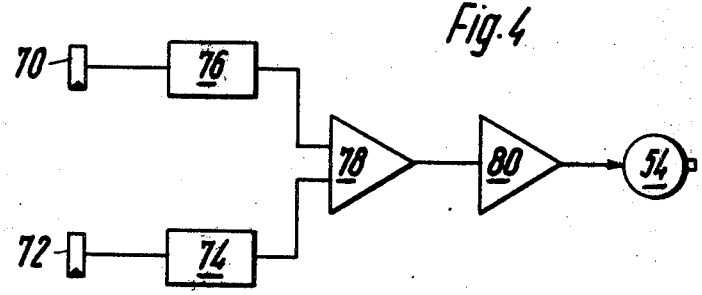
FIG. 4 is a block circuit diagram of a photoelectric follow-up control system according to the invention.

In FIG. 4 a block circuit diagram of a photoelectric follow-up control system has been shown, one of which is provided in each case for the axes of pivots 34 and 36. In order not to overburden the illustration, FIG. 4 simply carries references pertaining to the axis or pivot 34. The photoelectric cells 70 and 72 are connected to selective circuits 74 and 76 which are tuned to the modulation carried by the light emitted from the spotlamp 16. The circuits 74 and 76 can be designed as filters, e.g., resonance filters. By means of the circuits 74 and 76 the influences of daylight or other light sources, to which the circuits 74 and 76 are not tuned, can be isolated from the follow-up control systems.

The outputs of the circuits 74 and 76 are taken to a bit circuit or to a differential amplifier 78, which in turn feeds an ensuing power amplifier 80 which supplies or controls the motor 54.

When the individual spotlamps 18 to 24 are precisely aligned on the area 38 illuminated by the pinpointing spotlamp 16, the voltages at the outputs of the photoelectric cells 66, 68 and 70, 72 are matched to one another. The differential amplifier 78 then ceases to produce any control voltage to the amplifier 80 so that the motor 54 ceases to receive a voltage, in its turn, and thus comes to a halt.

If the illuminated area 38 is moved by shifting the pinpointing spotlamp 16, then the voltages at the outputs of the photoelectric cells 70 and 72 will differ from one another. The differential amplifier 78 will supply a voltage to the amplifier 80, and this will in turn be amplified. The motor 54 will therefore have a voltage applied to it and start rotating. The motor 54 rotates until the photoelectric cells 70 and 72 are uniformly illuminated by the area 38, and therefore produce identical output voltages. In this case, the differential amplifier 78 supplies no voltage to the amplifier 80. This condition corresponds with the desired alignment of the individual spotlamps on the area 38 illuminated by the pinpointing spotlamp 16.

During follow-up on the part of the spotlamps 18 to 24, their light sources are switched off. This avoids any unwanted optical disturbance of the photoelectric cells 66 to 72. Once a specific area 38 has been chosen, the control lever 30 is replaced in its inoperative position. This results in the switching on of the light sources of the spotlamps 18 to 24, and in the switching off of the follow-up systems. The motors 54 and 60 therefore cease to be supplied with voltage. Under conditions of full illumination, therefore, undesired displacements of the individual spotlamps 18 to 24 are avoided. Furthermore, by means of the follow-up control circuit shown in FIG. 4, very accurate adjustment of the spotlamps 18 to 24 to the illuminated area 38, can be achieved.

We claim:

1. An illumination system, comprising, in combination:
    a plurality of spotlamps each of which is separately and independently pivotably mounted and separately and independently driven;
    said plurality of spotlamps including a pinpointing spotlamp and several individual satellite spotlamps;
    said pinpointing spotlamp being adjustable to select a desired area to be illuminated;
    said pinpointing spotlamp being disposed substantially perpendicularly above an operating table within the confines of which said area to be illuminated is disposed;
    said individual satellite spotlamps being suspended at different and varying distances from said operating table;
    each said satellite spotlamp being provided with a photoelectric servomechanism including a follow-up control system which operates in response to light from said area illuminated by said pinpointing spotlamp to adjust the associated satellite spotlamp;
    said illumination system including means for switching off the satellite spotlights and switching on the follow-up system to avoid unwanted optical disturbance of the photoelectric mechanism.

* * * * *